(12) United States Patent  
Crowson et al.

(10) Patent No.: US 9,918,872 B1  
(45) Date of Patent: Mar. 20, 2018

(54) SYSTEMS AND METHODS FOR TREATING UTERINE ATONY

(71) Applicants: James Daniel Crowson, McKinney, TX (US); Jack Alfred Stecher, Dallas, TX (US)

(72) Inventors: James Daniel Crowson, McKinney, TX (US); Jack Alfred Stecher, Dallas, TX (US)

( * ) Notice: Subject to any disclaimer, the term of this patent is extended or adjusted under 35 U.S.C. 154(b) by 1210 days.

(21) Appl. No.: 13/899,838

(22) Filed: May 22, 2013

Related U.S. Application Data

(60) Provisional application No. 61/746,150, filed on Dec. 27, 2012.

(51) Int. Cl.
  *A61M 25/04* (2006.01)
  *A61F 7/00* (2006.01)
  *A61F 7/12* (2006.01)

(52) U.S. Cl.
  CPC .............. *A61F 7/0085* (2013.01); *A61F 7/12* (2013.01)

(58) Field of Classification Search
  CPC .... A61M 2025/1061; A61M 2025/109; A61M 2039/082; A61F 7/0085; A61F 7/12
  See application file for complete search history.

(56) References Cited

U.S. PATENT DOCUMENTS

| | | | |
|---|---|---|---|
| 6,645,233 B1 * | 11/2003 | Ayers | A61F 7/123 607/105 |
| 9,125,687 B2 * | 9/2015 | Yoon | A61B 10/0048 |
| 2003/0236546 A1 * | 12/2003 | Packer | A61B 17/12099 606/193 |
| 2005/0015047 A1 * | 1/2005 | Shah | A61M 25/1011 604/101.02 |
| 2008/0215031 A1 * | 9/2008 | Belfort | A61B 17/12099 604/500 |

* cited by examiner

*Primary Examiner* — Linda Dvorak  
*Assistant Examiner* — Yasamin Ekrami  
(74) *Attorney, Agent, or Firm* — Jeffrey Roddy

(57) ABSTRACT

A system for treating uterine atony, and promoting contraction of a uterus includes a heat transference article having a chilled surface in contact with an inner or outer surface of the uterus for a length of time sufficient to promote contraction while avoiding tissue damage. A heat transference medium such as a chilled saline solution, or cold gel is introduced to the article by injection, pre-filling, immersion or other suitable means, and is circulating or non-circulating.

10 Claims, 8 Drawing Sheets

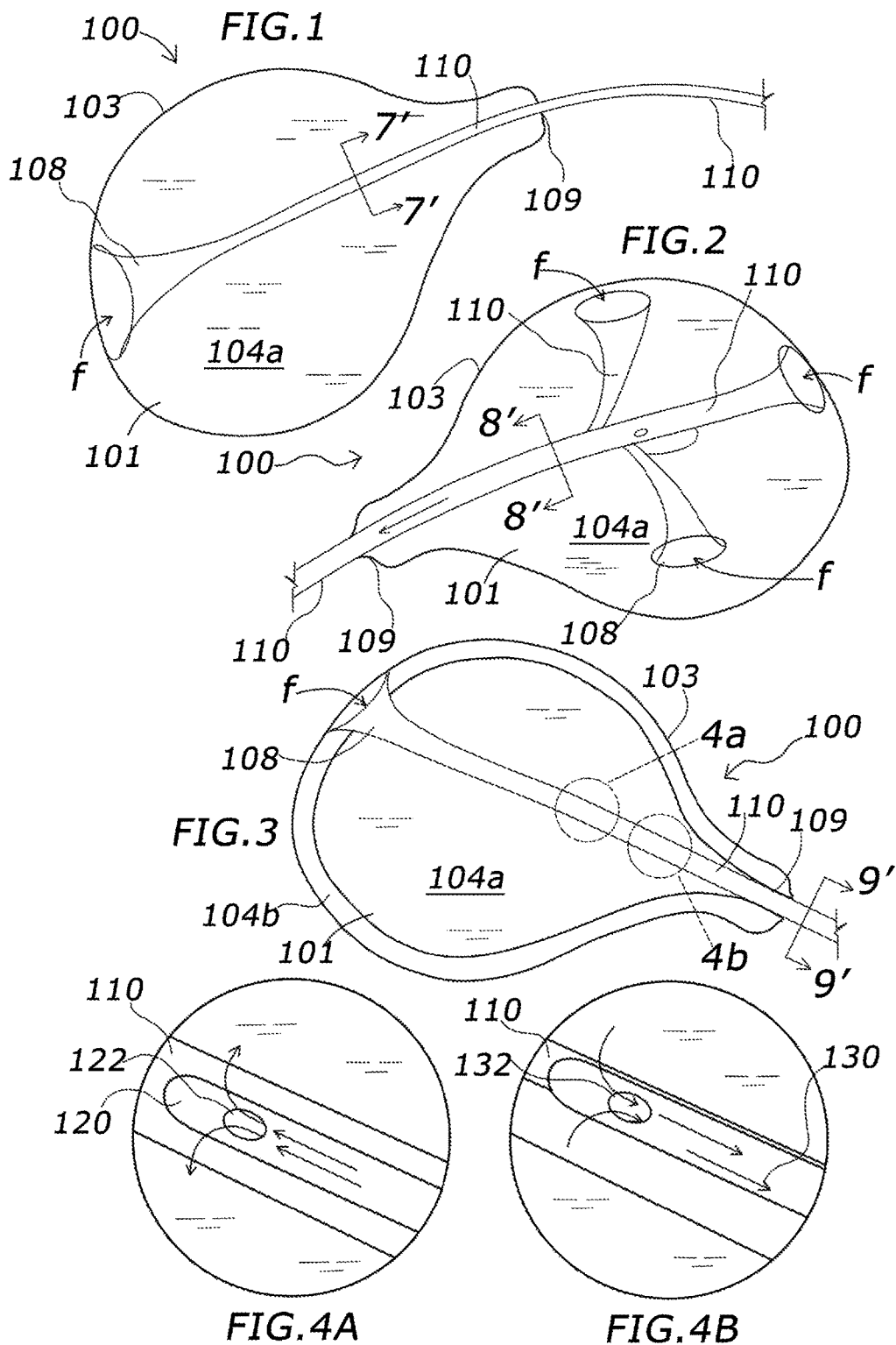

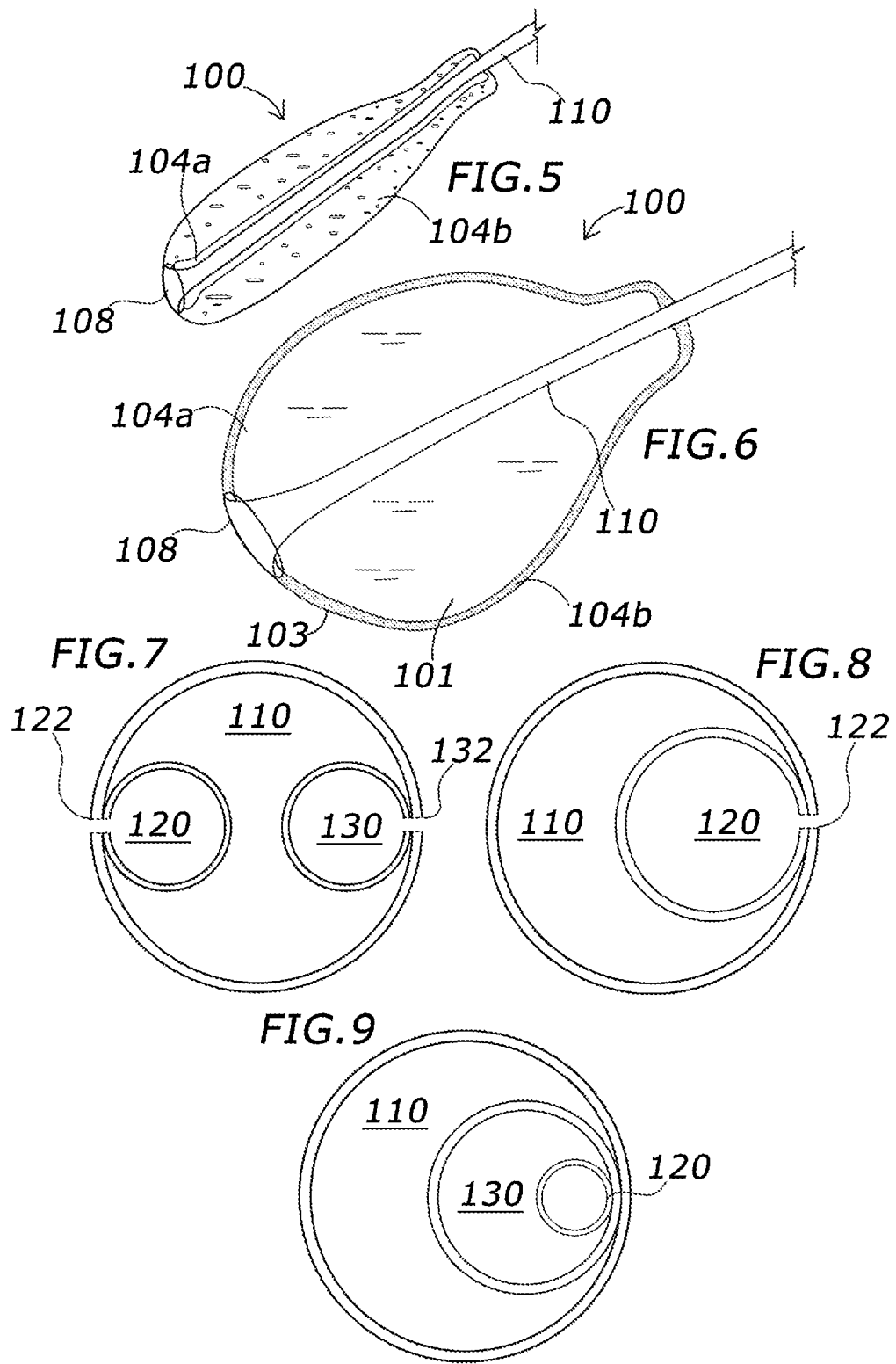

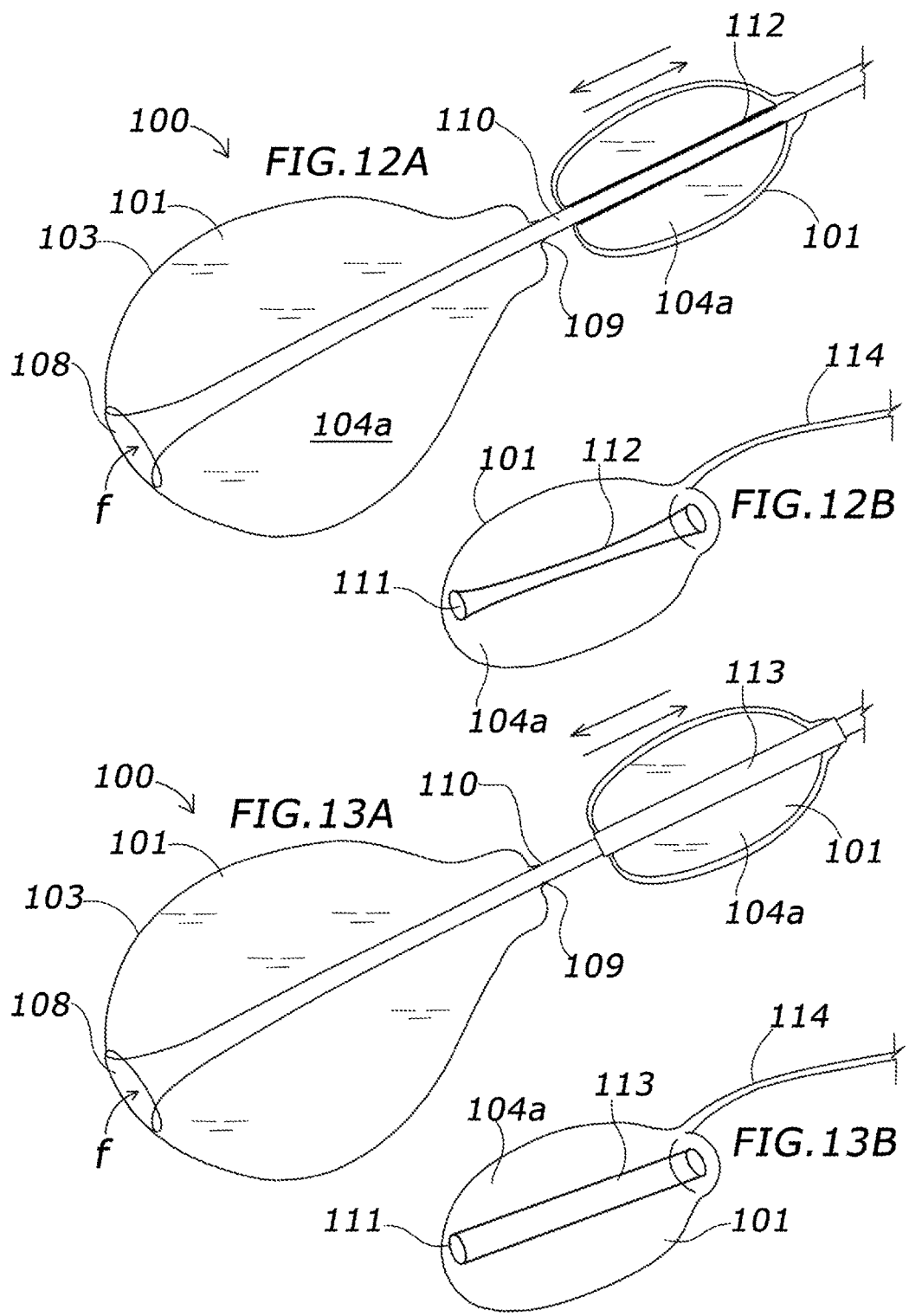

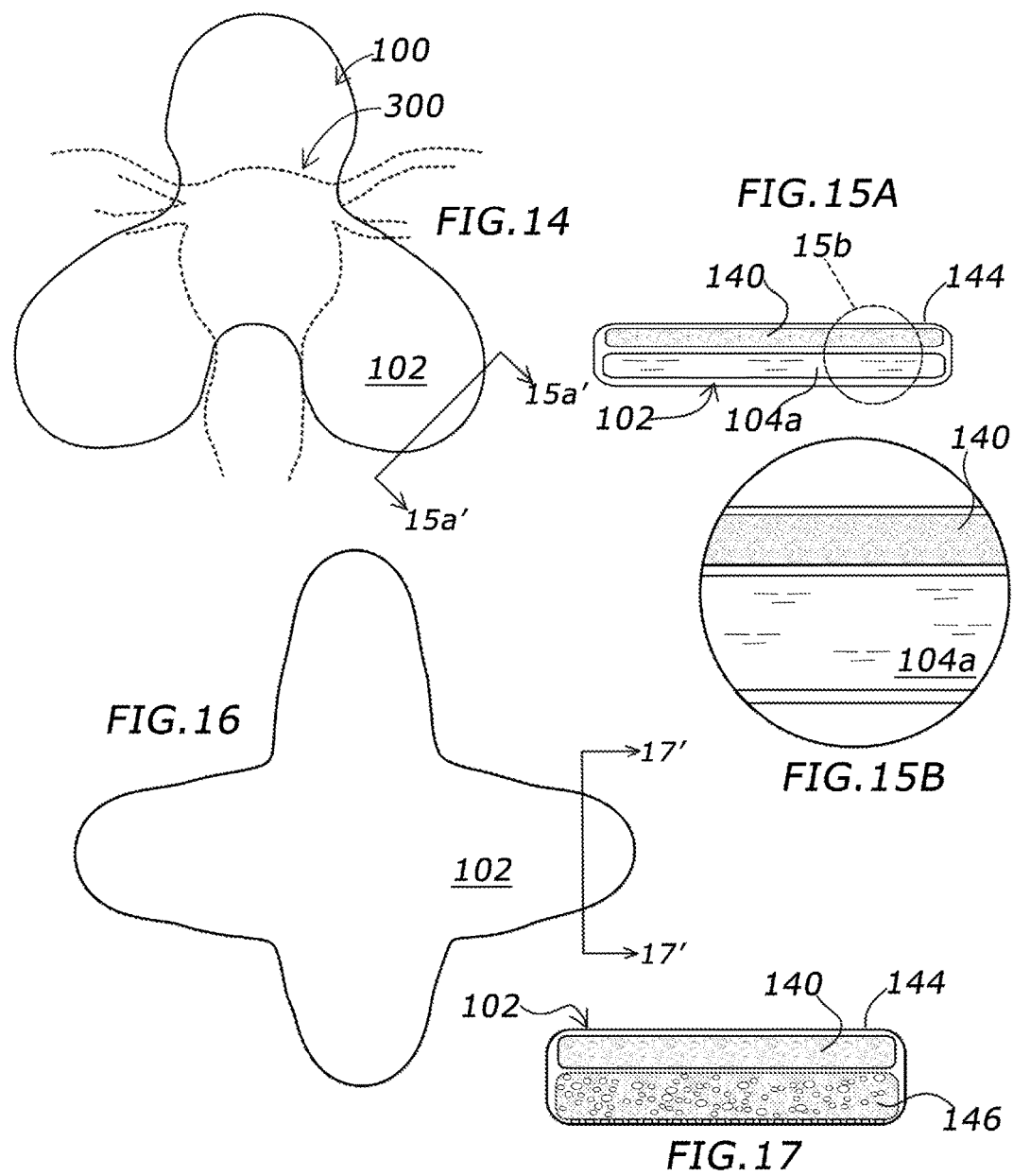

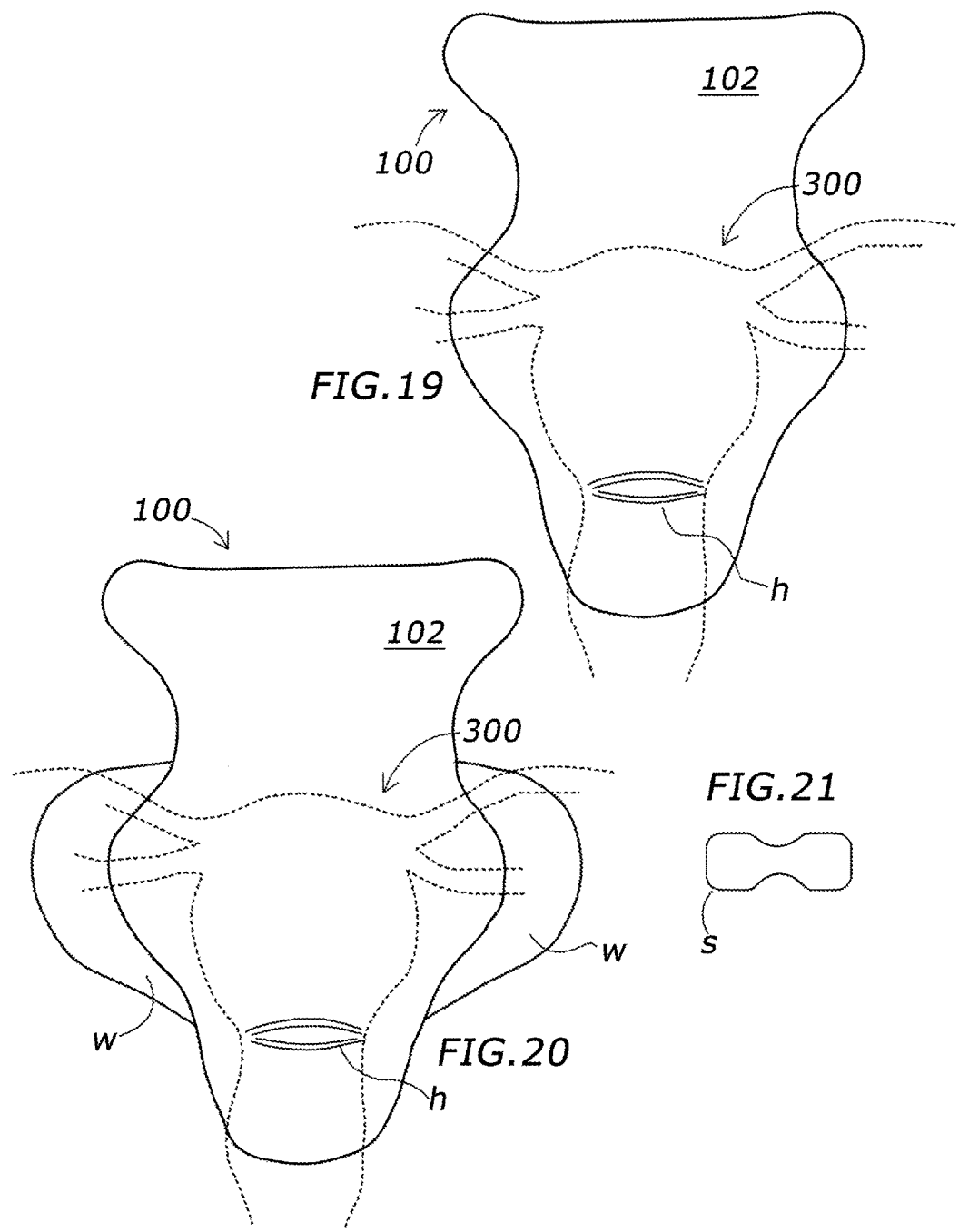

SYSTEMS AND METHODS FOR TREATING UTERINE ATONY

CROSS REFERENCE TO RELATED APPLICATIONS

This Application claims the benefit of U.S. Provisional Patent Application No. 61/746,150 filed Dec. 27, 2012.

FIELD

The present invention relates generally to systems for treating postpartum hemorrhage, vaginal bleeding, and more specifically, the application of non-necrotizing hemostatic means to an atonic uterus or vaginal vault.

BACKGROUND

Uterine atony is a failure of the uterine muscles to contract following delivery, whether by normal vaginal delivery or caesarean section, and represents the most common cause of postpartum hemorrhage (PPH). Currently, there are 130 million deliveries a year, worldwide and 4 million a year in the United States. 33% of the delivers in the U.S. occur via a caesarean section. Currently, approximately 960 maternal deaths occur per year in the United States with 25% of maternal death due to hemorrhage. Presently, treatment for PPH is substantially pharmaceutical in nature, and includes, the administration of oxytocin (Pitocin, Syntocinon), ergot derivatives such as Ergometrine and Methergine, and Carboprost (Hemabate), and various synthetic prostaglandins such as Misoprostol. While pharmacologic treatments for uterine atony do work well in many cases, there are still disadvantages. Patients can have a contraindication to a standard pharmacologic agent. For example, ergot derivatives are contraindicated in hypertensive patients. Other medications are not recommended for patients with asthma. Pitocin has been shown to cause cardiac collapse, hypotension, chest pain and headaches.

More recently, as an adjunct to pharmacologic agents, bladder tamponades such as the Bakri catheter have gained acceptance in clinical settings. Typically, such balloons are expandable by means of a saline injection into the body of the bladder. While a laudable addition to available treatments, efficacy for bladder tamponades of this type is not well established. Accordingly, it would be desirable to provide a non-pharmacological solution that can be used alone or in combination with other pharmacological and non-pharmacological modalities to control uterine atony and thereby control or prevent bleeding after a cesarean section or other procedure.

SUMMARY

The present invention seeks to address the condition of uterine atony among others, by intrauterine and/or extra-uterine application of cold and cooling articles which are brought into contact with the uterine surface in order to induce and promote contraction of uterine muscle. Application of the disclosed chilled articles in contact with the uterine surface will via thermal conduction, also minimize blood loss and facilitate the cessation of bleeding. Vaginal bleeding as a result of trauma can also be effectively treated using the methods and devices of the instant invention.

In one aspect, the instant invention is practiced with intrauterine articles which are placed through and within the vagina and into the uterus following a vaginal delivery.

In another aspect, the instant invention is practiced with articles applied to the external surface of the uterus and/or supporting tissues during a cesarean section or other gynecologic procedure.

In another aspect, the instant invention is practiced with articles inserted into the uterus via a hysterotomy site during a cesarean section to be temporarily maintained in place. Generally, if inserted into the uterus through an incision, tubing for fluid circulation, if any is present, will exit through the vagina.

In whatever aspect, an objective of the system is to promote cooling of the uterus and/or vaginal tissue in order to produce uterine contraction, promote and maintain tonicity of the uterus, and stop hemorrhage due to delivery or other trauma.

Other possible uses combining the disclosed aspects and features of the instant invention will suggest themselves to those having skill in the art, and are considered to be encompassed by this disclosure.

For intrauterine and/or vaginal application of the present invention, certain articles for the application of cold are considered to be particularly efficacious, and can include a reversibly expandable bladder constructed to distensibly conform to the uniqueness of an individual's shape whether uterine or vaginal. The bladder has at least one region that contains a circulating or non-circulating fluid. The bladder is medical grade silicone, polyurethane or other suitably expandable polymer as will be appreciated by those having skill in the art and benefit of this disclosure. The material of the walls of the bladder is selected according to its thermal conductivity in order to transfer heat from tissues into the heat sink of the bladder. While peripheral wall thickness of the bladder may vary when expanded depending on the elasticity of the material, in an unexpanded state the bladder wall thickness is preferably between and 09 mm and 10 mm. If the bladder wall includes an elastic material, A-scale shore durometer of the material is preferably between 10 and 60. However, because the material selected will depend in part on the specific gravity of the intended working fluid introduced into the bladder or other properties of the working fluid, elasticity of the material can vary. The working fluid is preferably chilled prior to introduction to the bladder in order to reduce the temperature of the bladder surface, or, in the cases in which the bladder possesses a separate peripheral cavity filled with a chilled media such as an icy-slush or cold gel, the working fluid can be introduced at or near normal room temperature in order to cause the chilled periphery of the bladder to distend, conform to, and contact an intrauterine surface. The bladder has an inlet for the introduction of at least one working fluid, whether chilled or not, and can possess an separate outlet with a pressure relief valve for the expulsion of excess fluid, wherein the relief valve is responsive to progressive contracting of the uterine muscles being induced by the application of the cold to the uterine surface. The bladder can also combine fluid introduction means and fluid expelling means in a single conduit, e.g., a tube with a port for fluid introduction and outlets communicating with the bladder interior whereby fluid is pushed backwards out the port which is typically equipped with a pressure relief valve, by induced uterine contractions. Temperature of the chilled media, whether ice, gel, fluid or slush is preferably above that which is known to cause tissue necrosis for the contemplated application times, but still capable of functioning as a heat sink in contact with uterine or vaginal tissue. While the chilled media is generally below room temperature and preferably at or just below the freezing point of water, the contacting surface of the bladder is preferably maintained between 0° Celsius and 10° Celsius, more preferably between 0° Celsius and 4° Celsius and even more preferably between 0° Celsius and 3° Celsius. The circulating or non-circulating fluid in the bladder is preferably a chilled solution such as chilled saline that has been cooled prior to introduction into the bladder by conventional refrigerative means, immersion in a chilled solution such as a icy slush, or by endothermic chemical reaction. There is a temperature gradient between a contacting surface of the bladder and the body tissue, such that the actual surface temperature of the bladder will vary from the temperature of the chilled media. For example, it is possible that the bladder surface can have a temperature higher than the chilled media so that the chilled media may be maintained at a sub-zero temperature to compensate for the buffering affect of the contacting surface. Contact time for the balloon depends on a number of factors including the temperature of the contacting surface, but can be anywhere in the range of 5 minutes to 5 hours depending on the contractility of the uterus.

As shown in FIGS. 12A-13B, two bladders can be paired in tandem for contact with both the vaginal vault and intrauterine surfaces.

Bladders can be selected for size depending on the specific application. In case of a caesarian section, the bladder can be inserted into the uterine cavity via hysterotomy incision, and maintained in contact against the intrauterine tissues.

In some applications, the bladder can possess for example, a wall of woven mesh with inner or outer surfaces covered by an impermeable polymer selected primarily for flexibility. The bladder in this case, would have relatively limited distension compared to the bladders constructed of elastic materials.

For extrauterine application of the present invention, for example, when a uterus is externalized during a caesarian section, certain articles for the application of cold are considered to be particularly efficacious, and include a chilled article that can be shaped somewhat like an incomplete pouch or lobate shroud for the partial enclosure, or binding of the externalized uterus. Like the bladder, the shroud is a support vehicle for a cold medium. The shroud possesses a cavity like the bladder, that is filled with circulating cold fluid, or non-circulating cold fluid. The cavity of the shroud can contain an absorbent medium. The shroud can include an inlet for the introduction of the cold fluid, or the addition of a fluid, such as a saline solution at normal room temperature that reacts with a chemical introduced to, or contained in a cavity of the shroud, to produce an endothermic reaction. It is conceivable that one or more cavities within the shroud can be distended by means similar to the bladder, in order to place additional pressure on the partially enveloped externalized uterus The shroud can include an absorbent layer such as a fiber or sponge for soaking up cold fluids prior to its contact with the uterine surface.

Whatever the vehicle, the temperature of the surface in contact with the uterus is preferably above that which is known to cause tissue necrosis for the contemplated application times, but still capable of functioning as a heat sink in contact with uterine or vaginal tissue.

In order to aid surgical staff, a thermal barrier can reside between the cold surface of the shroud and the surface being contacted by a surgical staff member, as for example, when the staff member is applying manual pressure to portions of the shroud in contact with the uterus.

The foregoing and other objects, features, and advantages of the invention will become more apparent from the following detailed description, which proceeds with reference to the accompanying figures.

BRIEF DESCRIPTION OF THE DRAWINGS

FIG. 1 is a perspective view of a heat transference article according to the present invention;

FIG. 2 is a perspective view of a heat transference article according to the present invention;

FIG. 3 is a perspective view of a heat transference article with annuli 108 as conduits for waste such as blood and tissue (f);

FIG. 4a is a detail view of a section of flow tube 110;

FIG. 4b is another detail view of a section of flow tube 110;

FIG. 5 is a perspective view heat transference article having plural cavities while in an unexpanded state;

FIG. 6 is a perspective view heat transference article having plural cavities while in an expanded state;

FIG. 7 is a sectional view taken along lines 7'-7' of (FIG. 1);

FIG. 8 is a sectional view taken along lines 8'-8' of (FIG. 2);

FIG. 9 is a sectional view taken along lines 9'-9' of (FIG. 3);

FIGS. 12A, 12B, 13A and 13B show tandem heat transference articles including an intrauterine bladder and a bladder for placement in the vaginal vault;

FIG. 14 is a plan view of a heat transference article shaped and sized to envelop an externalized uterus;

FIG. 15A is sectional view taken along lines 15a'-15a' of (FIG. 14);

FIG. 15B is a detail taken from 15A;

FIG. 16 is a plan view of a heat transference article shaped and sized to envelop an externalized uterus;

FIG. 17 is a sectional view taken along lines 17'-17' of (FIG. 16);

FIG. 19 is a plan view of a heat transference article shaped and sized to envelop an externalized uterus in which the uterus is atop the heat transference article;

FIG. 20 is a plan view of a heat transference article shaped and sized to envelop an externalized uterus in which the uterus is atop the heat transference article;

FIG. 21 shows a strap that can be used to hold a heat transference article in position about an externalized uterus;

DETAILED DESCRIPTION OF THE INVENTION

Figure 10:
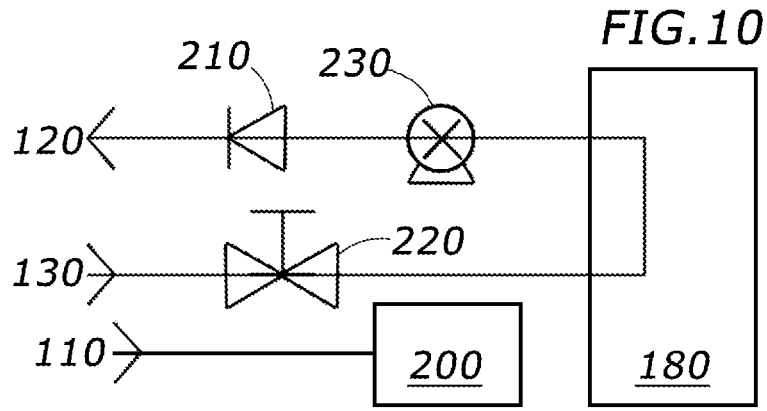
FIGS. 10-12 are diagrams showing typical fluid control means according to the present invention.

Reference Listing 100 heat transference article
101 bladder
102 shroud
103 wall
104a inner cavity
104b cavity
108 annulus 109 flow tube exit
110 flow tube
120 inflow tube
122 inlet
130 outflow tube
132 outlet
140 insulating material
142 perforations
144 poly layer
146 absorbent
180 chilled fluid source
190 fluid overflow
200 waste
210 non-return valve
220 pressure relief valve
230 pump
300 uterus Definitions In the following description, the term "outer surface" refers to the outer surface of the uterus which is accessible following caesarian section. The term "inner surface" refers to the inner surface of the uterus or the vaginal vault which is accessible following normal vaginal delivery or caesarian section. The terms "atony" or "atonic" refers to a lack of muscle contraction in the relevant tissue. The term "hemorrhage" and "bleeding" refers to uncontrolled bleeding whether of postpartum origin, or as a consequence of a gynecologic procedure. The term "expanding fluid", "distending fluid", "fluid for distending", "working fluid", or "chilled fluid" refers to a slush, liquid, gel or gas introduced into one of the devices of the system in order to increase or expand the contacting surface of an article or device, and/or serve as a thermal conductor. The term "chilled" as used herein, means any temperature below room temperature including chilled saline solutions. The term "contacting surface" refers to those surfaces of articles of the disclosed system which are placed in contact with an inner or outer surface of the uterus or vaginal tissue and other supporting structures. Unless otherwise explained, any technical or medical terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." Publications, patent applications, patents, and other references mentioned herein, if any, are incorporated by reference in their entirety for all purposes. In case of conflict, the present specification, including explanations of terms, will control. In addition, the materials, methods, and examples are illustrative only and not intended to be limiting.

Referring generally to FIGS. 1-21, for gynecological use, articles and methods comprising a system for applying non-necrotizing hemostatic temperatures to traumatized tissue for a time duration sufficient to control or stop bleeding and promote uterine contraction, include at least one article for contact with bleeding or atonic tissue, a chilled medium in at least one cavity of the article for heat conduction, a surface presenting a cold surface against the target tissue and serving as a heat sink, and wherein the article is applied to an inner surface or outer surface of a uterus. The following description includes examples of preferred embodiments and methods for using the particular articles employed in the system.

Referring generally to FIGS. 1-9 and 12A-13B a heat transference article to induce an atonic uterus to contract includes a bladder 101 for intrauterine applications with at least one cavity suitable for the introduction of chilled media, a flow tube 110 extending from a proximal end of the bladder and terminating in at least one annulus 108 that opens exteriorly to the bladder. The flow tube includes (1) a drain for waste tissue and body fluid (f) entering the at least one annulus, (2) an inflow means which is typically an inflow tube 120 possessing at least one aperture 122 opening into; and communicating with the bladder cavity for the introduction of chilled media by a syringe or pump (FIGS. 10-12) 230 such as a chilled saline solution or other chilled working fluid at pressures sufficient to expand the bladder walls which may be distensible or non-distensible. The bladder is comprised of elastic or inelastic material or a combination of elastic and inelastic materials. In cases where the bladder walls are elastic, tubing within the bladder is typically resilient, but less elastic than the walls. Materials having sufficient thermal conductivity to serve as a heat sink when applied to the inner surface of the uterus are suitable such as medical grade polyurethane, silicone, various elastomers, or biocompatible woven materials. The flow tube also includes (3) an outflow means which includes at least one aperture 132 communicating between the outflow tube 130 and the bladder cavity in order to drain excess working fluid which is mechanically or manually extracted or expelled by pressure exerted on the bladder by a contracting uterus. The working fluid within a bladder cavity is chilled to the desired temperature by refrigerative means, slush bath, or any other chilling means as will be appreciated by those skilled in the art.

While automated or manual fluid circulating means can be employed, it is possible that a one time introduction of chilled fluid into a bladder cavity while in situ is sufficient to stop bleeding of the tissue, and induce and promote contractions of the uterus. Alternately, the in situ bladder can be filled, emptied and refilled multiple times in order to (1) evacuate warmed fluid (2) maintain the desired temperature of the working fluid and (3) produce the desired effect of promoting contraction.

Turning to FIG. 1, a perspective view of an embodiment according to the present invention shows a heat transference article including a bladder which is filled with a chilled solution via flow tube 110. The article is typically introduced into the uterus vaginally in an unexpanded state and then filled with chilled fluid which is either circulating or non-circulating or alternately circulating and non-circulating.

FIG. 2 shows a heat transference article including a bladder with annuli 108 forming channels for the draining of uterine blood and tissue. While the bladder possesses one annulus at its distal end and 3 annuli generally spaced at 120 degrees circumferentially about the bladder, persons having skill in the art and benefit of this disclosure, will appreciate that various positions for the annuli are conceivable in order to effectively drain waste fluids such as uterine blood and shed tissue. It is also conceivable that the exterior surface of the bladder possess channels (not shown) that will serve as guides directing uterine blood and tissue waste to the annuli or single annulus. Such channels may radiate from the juncture between each annulus and the exterior surface of the bladder. It is also conceivable that the inner surface of the bladder cavity possess radiating tubing formed thereon, and the tubes possess apertures communicating with the outside of the bladder for the collection of uterine waste fluids. Accordingly, the instant invention is considered to encompass such alternate configurations.

FIG. 3 is a perspective view of an embodiment according to the present invention showing a heat transference article having a bladder with a first cavity 104a which is filled with a chilled medium either by manual, mechanical or automated introduction. The chilled medium can be circulating or non-circulating. A second cavity 104b can be pre-filled with a medium which is chilled through freezing such as a cold pack gel, or a saline solution. Note that expansion of the bladder to sufficiently contact the endometrium would still rely on the introduction of chilled fluid to the first cavity 104a to expand the peripheral cavity.

FIG. 4A is a detail view of FIG. 3 (4a), which shows inflow tube 120 situated inside flow tube 110, with the respective transported fluids segregated. Outlet 122 forms a conduit between the inflow tube and bladder cavity 104a. Similarly, FIG. 4A shows outflow tube 130, situated inside flow tube 110, with the respective transported fluids segregated. Inlet 132 forms a conduit between the inflow tube and bladder cavity 104a whereby fluids are extracted or expelled under pressure.

Regarding FIGS. 4A and 4B, it should be noted that the placement of the inflow and outflow tubes in relation to the flow tube can be applied to any of the embodiments herein. The inflow and outflow tubing can include a single aperture to draw or expel fluid as shown, or multiple apertures. Also, the particular placement of inflow and outflow tubing depicted is merely exemplary, and other configurations, for example, in cases where either inflow tube or outflow tube is external to the flow tube will be appreciated by those having skill in the art and benefit of this disclosure. Accordingly, the instant invention is considered to encompass such alternate placements.

Turning to FIGS. 5 and 6, similar to the bladders shown in FIGS. 1-2, a peripheral cavity 104b or chamber of a bladder can be filled with a fluid medium such as, but limited to normal saline, or an icy slush that is chilled prior to employment of the bladder. The slush can be a saline solution that has been chilled by conventional refrigerative means, a medium chilled by an endothermic chemical reaction similar to a cold pack, or other chilled medium having suitable thermal characteristics. Once the bladder is placed in the uterine cavity, inner cavity 104a is expanded by introducing a working fluid, whether a liquid or gas, whereby the cavity expands and increases the dimensions of the overall bladder. As the inner cavity 104a expands the material contained within the peripheral cavity 104b may thin. Each cavity of the dual cavity bladder can have a separate inlet and outlet (not shown) for respectively introducing and draining fluids. The article of FIGS. 5 and 6 shows respectively (1) a heat transference article prior to expansion possessing a bladder with a first cavity 104a for the introduction of a chilled medium therein and a second peripheral cavity 104b which is filled with a chilled medium such as a cold pack gel, or a saline solution, and, (2) the heat transference article of (FIG. 5) after filling with fluid in which the walls of the bladder have expanded and increased the surface area of the contents. Conceivably, the peripheral cavity may include a layer of insulative material such as an elastomeric foam in order to slow the rate at which heat is transferred from the uterine tissue to the working fluid contained in the inner cavity 104a.

FIGS. 7-9 are respectively, cross-sectional views taken along lines 7'-7' of (FIG. 1), lines 8'-8' of (FIG. 2) and lines 9'-9' of FIG. 3, and show various non-limiting configurations for inflow 120 and outflow 130 tubing relative to the main flow tube 110. In particular, FIG. 8 excludes the outflow tube in cases where the bladder is filled a single time or simply repeatedly filled and emptied with a chilled working medium. In this case, the inflow and outflow are combined in a single tube or conduit having an inline pressure relief valve that permits the expulsion of the chilled medium once the uterus begins to contract with sufficient force upon the bladder. While the pressure relief valve permits passive expulsion of the fluid contents by the contracting uterus, the contents still can be extracted by a syringe, pump or other means to evacuate the fluid. It should be noted that the inflow and outflow tubes can contain any number of inlets 122 and outlets 132 in communication with bladder cavity 104a.

Fluid Control

Figure 11:
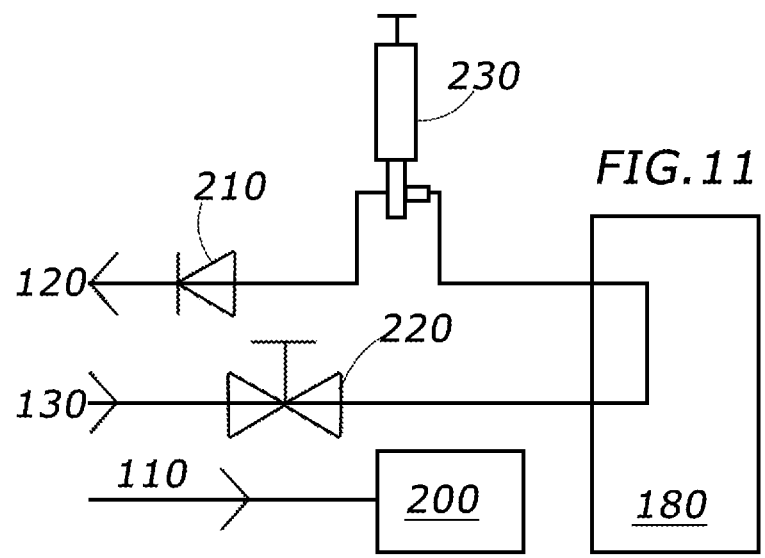
Figure 12:
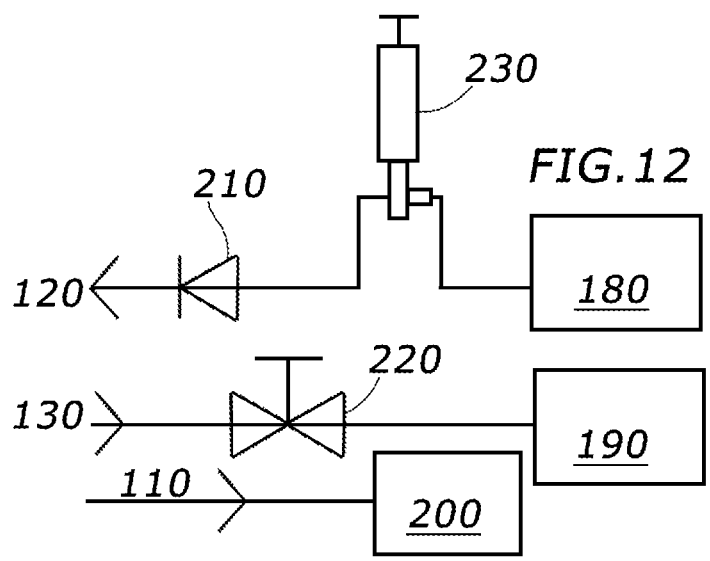

Referring generally to FIGS. 10-12, fluid control means applicable to any of the depicted embodiments includes (1) a conduit for chilled medium such as a chilled saline solution via inflow tubing 120 having an inline non-return valve 210 and injection means 230 which can be a pump; either automated or manually operated, with an adjustable pressure limit or a syringe for manually injecting chilled fluids, (2) a conduit for excess chilled medium including a pressure relief valve 220 inline with outflow tubing 130, and, (3) means for waste collection and re-directiong means including at least one annulus or aperture (FIGS. 1-4B) into which waste fluid and tissue can enter and thus be removed. The pump shown can be integrated with a chilled fluid reservoir 180 which can be a slush pot of chilled saline solution into which the pump is submerged, or, the pump can be inline with tubing drawing from a slush pot, or as an integrated part of a refrigerated system. Alternately, a bolus syringe with a ball valve switch enables the manual drawing up of a quantity of chilled fluid from reservoir 180 and pushing of the fluid into the bladder cavity. The pressure relief valve 220 can be anywhere inline the outflow tubing, whether immediately external to the bladder, or some distance away from the bladder at any location on the outflow tubing. FIGS. 10 and 11 depict fluid control means whereby chilled fluid is continually circulated into and out of the bladder. FIG. 12 depicts a non-circulating fluid control system in which outflowing fluid is neither re-chilled nor re-circulated. The fluid control means shown can be combined with any one of the embodiments shown without departing from the scope of the invention. Features and aspects previously described, and relating to the single cavity bladder such as valves, check valves and fluid cooling and fluid introduction and evacuation may be employed with bladders having plural cavities.

Turning to FIGS. 12A-13B, two expandable bladders can be used in tandem so that one bladder remains in the vaginal vault, while the other bladder resides in the uterine cavity. In this case, the vaginally placed bladder is expanded and cooled in the same manner as the intrauterine bladder. The intravaginal bladder will also prevent the intrauterine bladder from sliding out of position while the uterus and supporting tissues are being cooled to promote contraction and hemostasis. Because cooling the vaginal vault is thought to help with constricting blood flow through the uterine artery and branching vessels as they innervate the vaginal wall and tissues of the lower uterine segment, even if the vaginal vault is not bleeding, a bladder can be placed in the vaginal vault as an adjunct to treating the atonic uterus. FIGS. 12A-13A show heat transference articles including tandem intrauterine bladder and vaginal bladder 101, in which both bladders are coaxially aligned about flow tube 110. Bladder 101 has a central passageway 111 allowing the vaginal bladder to be slipped over flow tube 110 behind the larger intrauterine bladder. Like the remainder of the bladder, the passageway 111 lining is made of a material such as polyurethane or other polymer except having a greater relative shore value, so that when the vaginal bladder 101 is expanded by the injection of fluid, the passageway 111 is caused to constrict slightly about the flow tube providing a friction fit sufficient to resist unintended position shift, but permitting manual re-positioning. Alternately, a separate less resilient tubular sleeve 113 over which the vaginal bladder is placed, can be slid over the flow tube. When the vaginal bladder is expanded, passageway 111 is distended sufficiently to grab the sleeve. In this case, the clearance between the sleeve and the flow tube remains the same irrespective of the expansion of the vaginal bladder and is sufficient to permit positioning by friction fit along the flow tube, while resisting incidental and unintended movement. While FIGS. 12A-13b show tandem bladders, it should be noted that the bladders of the configuration can be used independently.

In some cases, vaginal tissue is affected by trauma causing the vaginal wall to hemorrhage. In such cases, a single bladder can be placed in the vaginal vault.

The exterior surface of the bladder(s) may include a hemostatic agent such as potato starch. When the bladder is expanded, the hemostatic agent would contact the uterine or vaginal surfaces.

Referring to FIGS. 14-18, a heat transference article with a chilled surface is wrapped about and over an exposed extrauterine surface in a case where the uterus has been externalized. A shroud 102 with a chilled medium is placed in intimate contact with the exterior surface of the uterus and supporting tissues to slow and ultimately stop blood loss, and induce and promote contraction of uterine muscle. On the side facing the uterus, the shroud has a outer cavity 104a containing the chilled medium which is covered by a material selected for desired thermal conductivity which can be a polyurethane 144 or other flexible polymeric shell. On the side facing away from the uterus, which is manipulated by surgical staff, the shroud includes a thermal barrier 140 which can be a water proof layer, a reflective layer of mylar, or an insulative layer of for example, flexible foam to prevent discomfort of hospital staff whose hands might contact the surface. The shroud can also include a reflective surface facing toward the thermal barrier to slow ambient heat conduction to the chilled medium. A reflective barrier can be placed between the cavity having the chilled medium and the insulative layer. It should be noted that the sectional views of FIGS. 15a and 17 are depicted with exaggerated thickness in order to better differentiate the layers, and particularly the absorbent 146 cavity and insulative layer. The thickness of the shroud is preferably anywhere form 2 mm to 2 cm—but can exceed 2 cm without departing from the scope of the invention.

Figure 18:
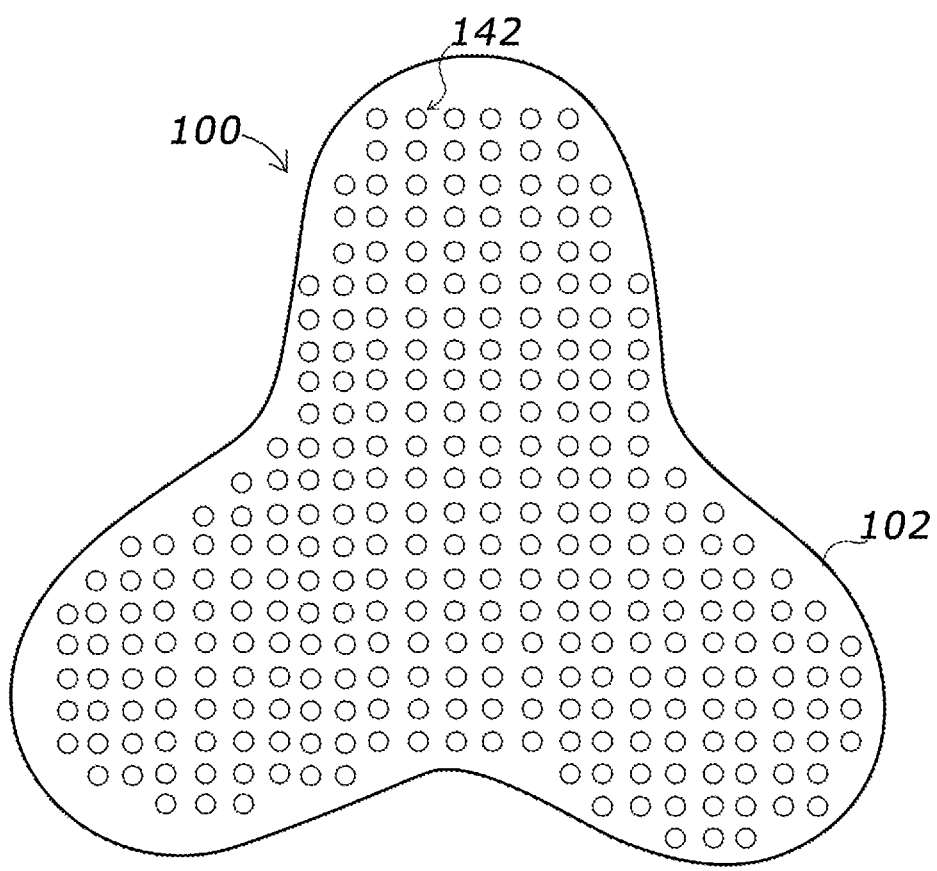
FIG. 18 is a plan view of a heat transference article shaped and sized to envelop an externalized uterus having perforations allowing the absorption of chilled fluid.

Like previously described embodiments, shroud 102 can include similar means for fluid introduction such as flow tube 110 coupled with a flow control methods previously described in order to further expand the cavity once the shroud is about the uterus. Like previously described embodiments, the cavity can include a pre-filled absorbent medium 146 within cavity 104a which converts to an semi-solid cold gel, or icy slush when the shroud is frozen. The pre-filled medium can be chilled by chemical endothermic means supplied with the medium. The cavity can be filled with an absorbent material such as a sponge or cellulose fibers, and the entire shroud dipped in a reservoir of chilled fluid for absorption into the cavity via fluid introducing openings such as perforations 142 (FIG. 18). Flexibility of the shroud and its ability to retain its shape depend on many factors including the chilled medium selected, and the thickness and flexibility of other shroud materials such as the insulating elements. Preferably, the thickness of the shroud is such that it can be draped over an externalized uterus. The shroud includes lobes (FIGS. 14, 16, 18, 19, 20 and 22) to permit wrapping and partial encapsulation of an externalized uterus when placed thereon as depicted in while avoiding undesired contact or pressure against/on adjacent tissue. Various portions of the shroud including multiple lobes, if any, can be divided from the rest of the shroud by laminated seams (not shown) that permit the shroud to fold easily.

Figure 22:
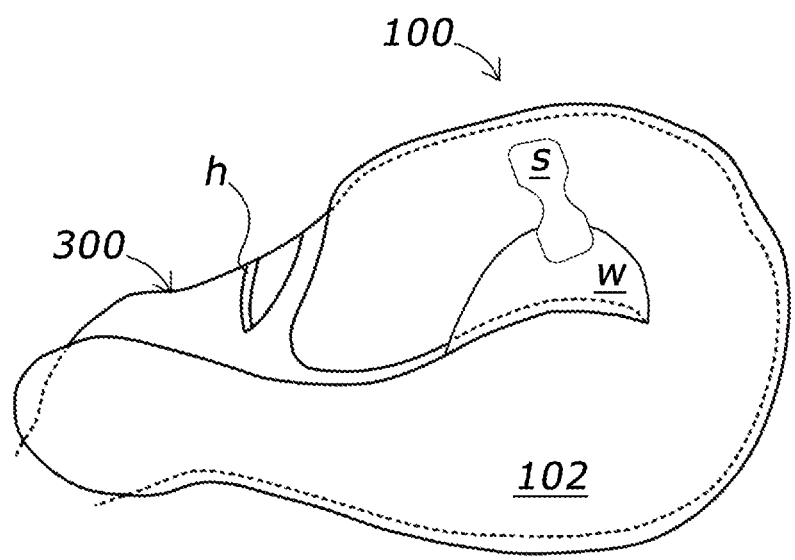
FIG. 22 is a side view of a heat transference article enveloping and binding an externalized uterus.

Moving to FIGS. 19 and 20, a heat transference article 100 includes a lobate shroud 102 shaped and sized to be placed against the posterior surface of an externalized uterus and cervix and wrapped thereover to provide cold temperatures in order to promote contractions. To increase contact pressure, the shroud can include elastic or stretchable wings (w) that are tensionably stretched over the wrapped uterus and secured by a strap (s) that can be adhesively applied, or for example, a via hook and loop fastener. Preferably, lobes of the heat transference article would be arranged so that the hysterotomy site (h) would remain accessible when the uterus is wrapped (FIG. 22). Contact times for the shroud and the uterus are preferably anywhere from 1 minute and 30 minutes.

It will be appreciated by those skilled in the art that features and aspects described earlier in this disclosure such as single and dual fluid filled cavities, pressure relief valves, check valves and fluid control means can be combined with the extrauterine shroud. For example, the shroud can possess single or plural cavities, and the fluid within the cavities can be static or circulating.

Where the shroud includes a cavity filled with a chilled solution such as a sterile saline derived slush, it can be used for cooling an externalized uterus by placing within the externalized uterus via a hysteromy site to be held there temporarily against intrauterine tissue by the hands. In this case, it can be used as a cold wipe to extract waste tissue. The cavity of the shroud can include an insulative outer layer to slow warming of the solution.

Applying cold to an atonic uterus in the manner set forth in this disclosure whether inside the uterine cavity or to the extrauterine surface, and whether by temporary contact with a chilled article or temporary contact with a chilled solution, will facilitate contraction and control bleeding. It should be noted that the instant invention is generally applicable to mammalian physiology, and should not be construed as being limited to use with human beings. In view of the many possible embodiments to which the principles of the disclosed invention may be applied, it should be recognized that the illustrated embodiments are only preferred examples of the invention and should not be taken as limiting the scope of the invention. Therefore, this disclosure is intended to cover such alternatives, modifications, and equivalents as may be included in the spirit and scope of the description in view of the appended drawings and claims.

We claim:

1. A heat transference article, comprising:
 a delivery body for at least one chilled medium which is conformable to a surface of the uterus further comprising:
 (I) at least one chill-able contacting surface defining a support for the chilled medium maintainable at a temperature sufficient to promote contraction of an atonic uterus, and a region for the retention of the chilled medium;

(II) at least one funnel-shaped annulus includes a flared opening that opens exteriorly to the delivery body and is contiguous with an outer surface of the delivery body, the flared opening tapers to a narrowed conduit wherein an outer surface of the narrowed conduit resides inside the bladder, and the at least one funnel shaped annulus is configured to face the surface of the uterus;

(III) at least one inlet tube for the introduction of fluids into the delivery body, and a drain tube contiguous with the narrowed conduit for the evacuation of waste fluids gathered from outside the delivery body via the at least one funnel shaped annulus.

2. The article according to claim 1, in which chilling of the medium is by a process selected from at least one of the following: refrigeration, endothermic chemical reaction, contact with a cold medium, immersion in a cold medium.

3. The heat transference article according to claim 1 including at least one lobe.

4. The heat transference article according to claim 1 tensionably applied to an inner surface of the uterus.

5. A heat transference article configured to conform to an interior surface of a uterus, comprising:

(1) a bladder for a chilled medium includes at least one funnel-shaped annulus, the at least one funnel-shaped annulus includes a distal end with a flared opening that is contiguous with an outer surface of the bladder and which opens exteriorly to the bladder, the flared opening tapers to a narrowed conduit, an outer surface of the narrowed conduit resides inside the bladder;

(2) in communication with the at least one funnel-shaped annulus, a flow tube defining a drain for waste tissue and body fluid entering the at least one funnel-shaped annulus; and, (3) an inflow tube configured to introduce a chilled medium into the bladder.

6. The heat transference article according to claim 5 wherein the flow tube contents and chilled medium are segregated.

7. The heat transference article according to claim 5 wherein the inflow tube is adjacent the flow tube.

8. The heat transference article according to claim 5 wherein the inflow tube is inside the flow tube.

9. The heat transference article according to claim 5 further comprising an outflow tube configured to remove the chilled medium.

10. The heat transference article according to claim 5 further comprising circulation of a chilled medium into and out of the bladder.

* * * * *